United States Patent [19]

Acker et al.

[11] 3,983,006
[45] Sept. 28, 1976

[54] METHOD FOR DETERMINING MINIMUM INHIBITORY CONCENTRATION OF ANTIBIOTIC

[75] Inventors: Jesse L. Acker, Rockaway, N.J.; Peter M. Meserol, E. Northport, N.Y.

[73] Assignee: Akro-Medic Engineering, Inc., Denville, N.J.

[22] Filed: Aug. 23, 1974

[21] Appl. No.: 500,125

Related U.S. Application Data

[62] Division of Ser. No. 290,654, Sept. 20, 1972, Pat. No. 3,837,745.

[52] U.S. Cl. .......................... 195/103.5 R; 195/127
[51] Int. Cl.² .......................................... C12K 1/04
[58] Field of Search .................... 195/103.5 R, 127; 424/8; 250/218; 356/36, 39, 180, 184, 186, 201, 204–207, 244, 246; 23/353 R, 259

[56] References Cited
UNITED STATES PATENTS

| | | | |
|---|---|---|---|
| 3,488,156 | 6/1970 | Good et al. | 23/253 R |
| 3,730,842 | 5/1973 | Wyatt et al. | 195/103.5 R |
| 3,772,154 | 11/1973 | Isenberg et al. | 195/127 |
| 3,832,532 | 8/1974 | Praglin et al. | 195/103.5 R |
| 3,895,661 | 7/1975 | Praglin et al. | 195/103.5 R |

OTHER PUBLICATIONS

Heman-Ackah, "Microbial Kinetics of Drug Action Against Gram-Positive and Gram-Negative Organisms" J. Pharmaceutical Sciences 63:7 (1974) pp. 1077–1083.

Garrett et al. "Kinetics & Mechanisms of Action of Drug on Microorganisms" J. Med. Chem. vol. 12, 1969, pp. 740–745.

*Primary Examiner*—A. Louis Monacell
*Assistant Examiner*—C. A. Fan

[57] ABSTRACT

A method of determining minimum inhibitory concentration (MIC) of an antibiotic by continuously measuring the change in optical properties in response to the bacterial growth rate of a bacterial suspension in the absence and the presence of the antibiotic. The method is carried out in an automatic biological fluid analyzer.

8 Claims, 10 Drawing Figures

METHOD FOR DETERMINING MINIMUM INHIBITORY CONCENTRATION OF ANTIBIOTIC

This is a division of application Ser. No. 290,654, filed Sept. 20, 1972, now U.S. Pat. No. 3,837,745.

BACKGROUND OF THE INVENTION

1. Field of the Invention

This invention relates to an apparatus and method for performing medical bacteriology and clinical chemistry by means of changes in turbidity, color or other optical properties which serve as indicators of biological activity, content or condition of the specimen under investigation. More particularly, this invention relates to an apparatus for automatically and continuously determining the rate of the bacterial growth by photometric means.

The specimen may be a biological fluid recovered from a patient, such as serum, plasma, urine, cerebrospinal fluid, acities or an artificially prepared nutrient or reagent fluid capable of supporting or demonstrating phenomena correlative to pathological, physiological, chemical, or metabolic state, activity or content.

Current clinical practice in medical microbiology and bacteriology is largely concerned with the isolation and evaluation of pathogenic bacteria from specimens of clinical interest. Such specimens may be derivative of both the patient, for example his blood, urine, wound exudate, or other biological fluid, or his immediate or etiological environment, such as food, air, water, or other factors of an infection or communicable disease vector system. Concomitant with the identification of a viral, mycotic, or bacterial pathogen agent in a specimen is the requirement for determining what antibiotic agent is effecive against a specific pathogen and to what degree it is effective in comparison to other chemotherapeutic agents available to the clinician as treatment of the condition.

Assay of biological fluids for levels of antibiotic, in vivo, also falls within the scope of medical microbiology, although the performance of the procedure is far less frequent than the above-described identifications of antibiotic effectiveness or sensitivity, a term derived from the subject organism's "sensitivity" to a drug. The assay procedure is extremely difficult to perform under presently available conditions in the laboratory and as such it is used only in research or in cases of extreme clinical importance. Although the information derived from such a procedure is very valuable to the clinician, it is an abnormally severe imposition on the laboratory staff.

The determination of minimum inhibitory concentration (MIC) of the antibiotic effectiveness against a particular pathogen also falls within the scope of medical microbiology, although not performed as often as antibiotic sensitivity.

DESCRIPTION OF THE PRIOR ART

Prior art identification procedures in the bacteriology laboratory are based on the taxonomic evaluation of cultures grown on solid or gelled media, immunofluorescent microscopic evaluation or color change of a nutrient media such that bacterial growth is indicated by reaction with metabolic products derived from such growth. Nutrient media can also be formulated to support the growth of specific pathogens or classes of pathogens to the exclusion of others and to indicate such growth by color change.

Recently there have been a number of attempts for meeting the need for automating the tedious manual methods for the determination of an organism's sensitivity. Although there are a number of automatic devices on the market, they have not efficiently solved the problems of cross-contamination between samples and the slow rate of analysis and they have not provided for a convenient means of random sample ingress and egress during the bacterial growth cycle. Because of their complexity, prior art automatic devices, require a great deal of maintenance and laboratory space.

Examples of such complex prior art devices which photometrically analyze specimens in a plurality of cuvettes are disclosed in several recent patents including Wood et al, U.S. Pat. No. 3,523,737 and Kuzel et al, U.S. Pat. No. 3,609,040. These devices contain a plurality of moving parts which require constant maintenance and decrease their reliability. There is a long-felt need for an apparatus utilizing photometric principles which is simplistic in design with almost no moving parts and with all operations carried out pneumatically and optoelectronically.

In an entirely different applicaton, i.e. the textile dyeing industry, than that of the present invention, a colorimeter has been described in Ward, U.S. Pat. No. 3,531,208, in which a plurality of dye samples are optically measured by means of a plurality of detectors and a plurality of amplifiers and the measurement is compared against a standard color chart. This reference is recited herein to show the general state of the colorimetric art.

SUMMARY OF THE INVENTION

The apparatus of the present inventon provides a biological fluid analyzer capable of antibiotic sensitivity testing and related procedures at a reduced cost in labor, time and expense, thus encouraging the clinician to use techniques heretofore considered impractical due to such costs.

The apparatus comprises:
a. a plurality of cuvettes,
b. a chamber for the fluid,
c. means for placing the chamber in fluid communication with each of the cuvettes and for permitting flow of fluid from the chamber into each of the cuvettes,
d. a plurality of optical transmitting means in registration with each of the cuvettes for transmitting a beam of radiant energy through each of the cuvettes, and
e. detector means for intercepting each of the beams of radiant energy and for measuring any optical change in the radiant energy passing through the fluid in each of the cuvettes.

The plurality of cuvettes and the chamber form a selfcontained cartridge of unitary construction which can be made inexpensively of a transparent rigid plastic e.g. polyvinyl chloride, polystyrene crystal and the like, thus making the entire cartridge disposable and eliminating repetitive use of nonexpendable equipment and eliminating the problem of cross-contamination of pathogenic specimens.

The chamber forms the upper portion of the cartridge which is filled with the growth or nutrient media. The plurality of small cells or cuvettes are in fluid communication with the larger chamber by a plurality of valve means positioned in the floor of the chamber above each of the cuvettes to permit unidirectional flow. When the cartridge is placed within a carriage housing the plurality of transmitting means and the detecting means, each of the cuvettes is in registration therewith.

Agitation means is provided for mechanically vibrating the complete carriage to effect agitation of the suspension. In addition, pneumatic means can be provided to permit aeration (bubbling) of the fluid in the chamber and cuvettes.

A suitable pneumatic connection is established between the disposable cartridge and the carriage housing the transmitting and detecting means. Upon an appropriate signal from the carriage, a differential pressure gradient is applied between the upper chamber and the lower cells and causes the contents of the upper chamber to flow to the lower ones. Gas permeable, liquid barrier means is in gaseous fluid communication with each of the cuvettes so as to permit the gas initially present in each of the cuvettes to escape from the cartridge when the unidirectional valves are open and to permit ease of flow of fluid from the chamber in order to completely fill the cuvettes, but prevents passage of liquid there through.

The method of the present invention comprises the following steps: (1) placing biological fluid, e.g. a bacterial suspension, in the chamber, (2) placing an array of biological challenge material, e.g. impregnated paper discs of lyophilized antibiotic agent, into at least a portion of the plurality of the cuvettes, (3) monitoring the changes in the optical properties of the fluid until at least the desired condition of the optical properties has been reached and then passing separate portions of the fluid into at least a portion of the cuvettes that contain the challenge material to produce an array of substantially identical fluid samples which are exposed to said array of biological challenge materials, and (4) evaluating the change in optical properties of the contents in each of the cuvettes.

As a result of step 3 above, for example, the antibiotic in the disc becomes rehydrated and forms an antibiotic and media/micro-organism suspension. The antibiotic titer is determined by the respective potency of the antibiotic in each of the cuvettes and the volume of each of the cuvettes which is constant in the apparatus of this invention. The bacterial growth rate, in this example, is evaluated by means of the plurality of individual optical detector systems each of which is in registration with its respective cuvette, or via one long detector in optical registration with all the cuvettes in the cartridge.

Electronic computation means such as computers and/or other computing devices well known in the art are available to evaluate the output of the detector means and to make the appropriate calculations either through analog or digital means to record and display the results in a meaningful and appropriate manner. These results include the changes in the growth rate in each cuvette, the relative changes between the control cuvette containing no antibiotic and the sample cuvettes and overall relationship between each of the cuvettes if necessary. The detectors are connected in common and their serial outputs go through a single electronic amplification channel to the computation means, whereas the sequencing of the observation interval is accomplished by serially energizing the light source circuitry or by multiplexing the light sources in accordance with pre-programmed instructions. The results from the observations are amplified, normalized, base-line corrected and digitized to facilitate their display in a clear and clinically meaningful format either by alphanumeric printing, chart recording and/or cathode ray tube displays which are well known to the art.

BRIEF DESCRIPTION OF THE DRAWINGS

The foregoing description of the present invention will become readily apparent when read in conjunction with the drawings in which.

DESCRIPTION OF PREFERRED EMBODIMENTS

Figure 1:
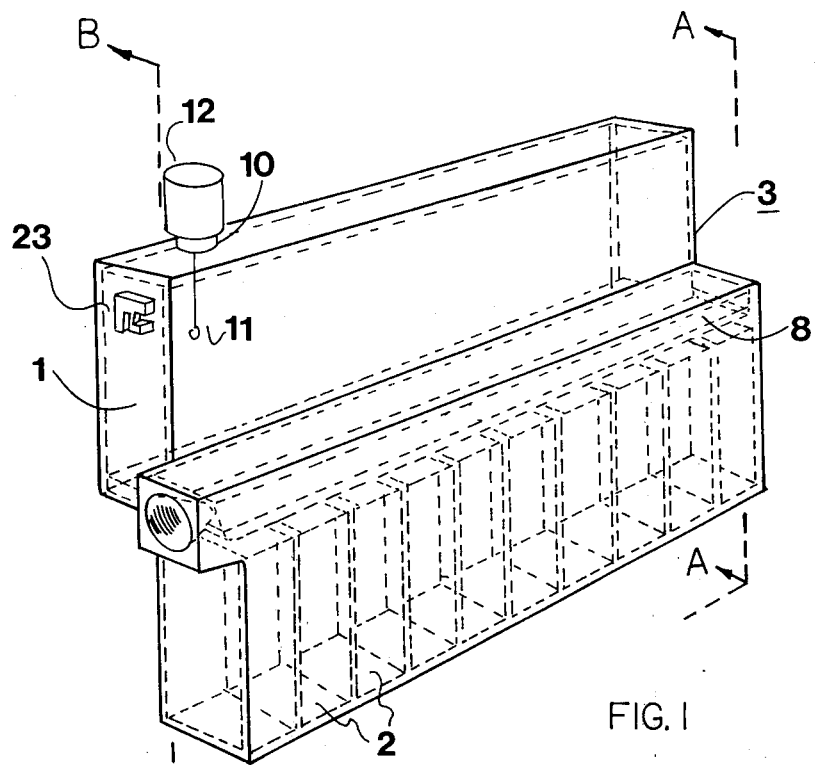
FIG. 1 is a general perspective view of the plastic disposable cuvette cartridge.
Figure 5:
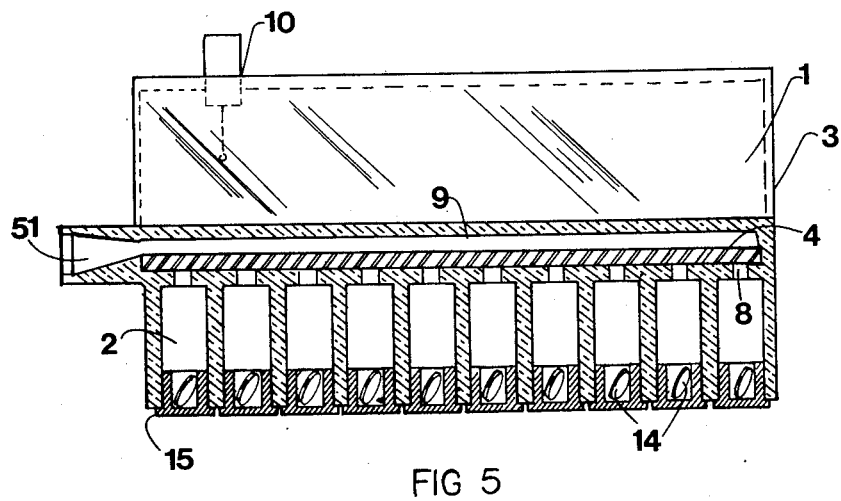
FIG. 5 is a sectional elevation of the cartridge taken along axis A—A in FIG. 1.
Figure 6:
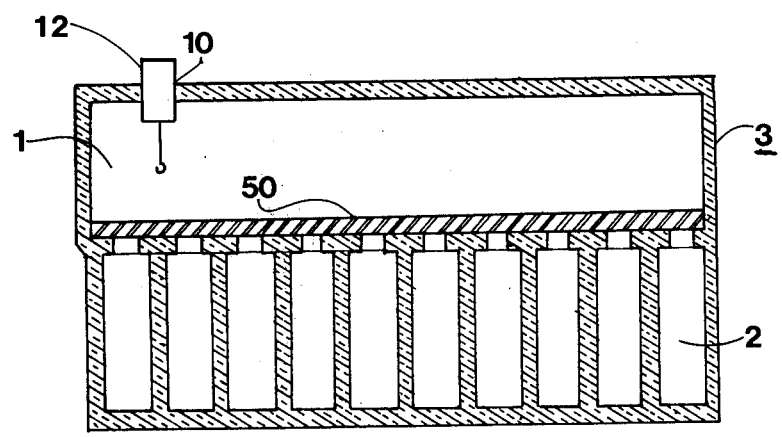
FIG. 6 is a sectional elevation taken along axis B—B in FIG. 1.

Referring now to FIGS. 1, 5 and 6, upper chamber 1 and the plurality of cuvettes 2 form disposable cartridge 3. Tubular channel 4 is shown positioned across the entire length of cartridge 3 and is in gaseous fluid communication with each of cuvettes 2 by means of orifices 8 and the fact that tube 4 comprises a gas permeable material, e.g., low density foamed polytetrafluorethylene. Tube 4 is within non-permeable channel 9. This critical feature of the present invention is described more completely below in connection with a discussion of FIGS. 2, 3, 7 and 8. Mounted on top of chamber 1 is inlet port 10 throughwhich is passed the biological fluid to be evaluated. Positioned within inlet port 10 is inoculating loop 11. For example, an isolated accession of the organism used in a given test is transported into chamber 1 via inoculating loop 11 through inlet port of cartridge 3 and is then isolated by means of cap 12. Discs 14 are impregnated to various concentrations with lyophilized antibiotic or other chemical reagent under evaluation and at least one disc is inserted into the relieved interior of each plug 15 which is positioned within each of cuvettes 2 as shown.

Figure 2:
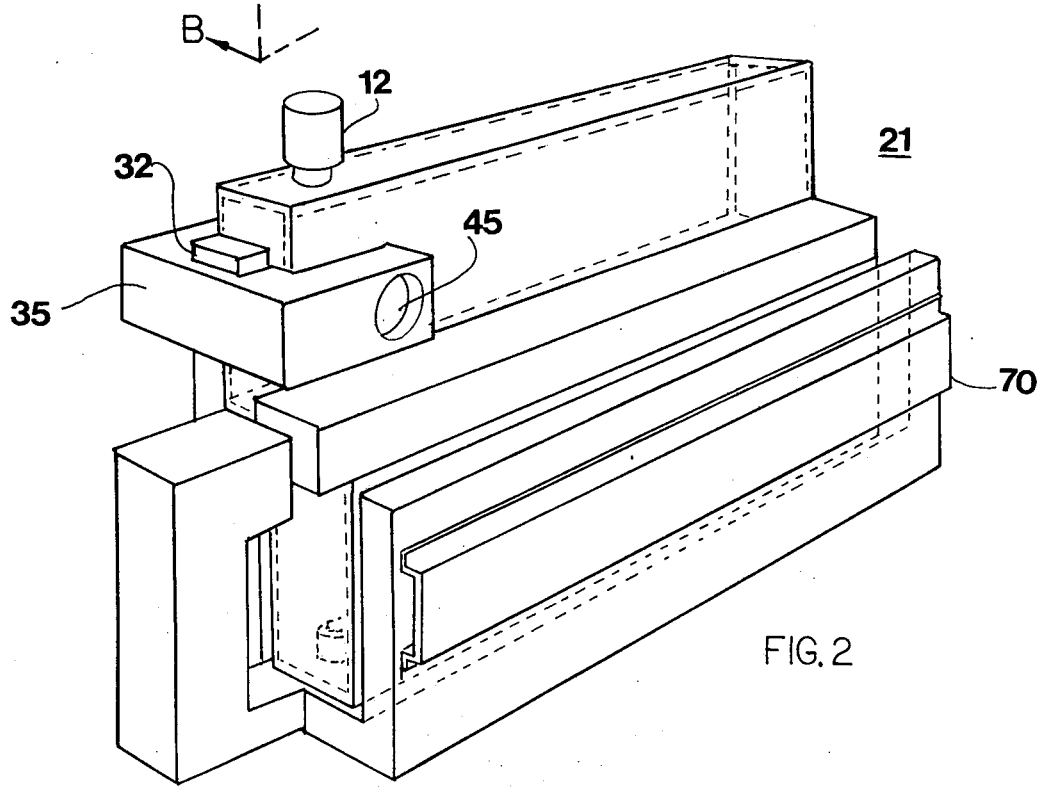
FIG. 2 is a general perspective view of the cuvette cartridge in place within a detection module.
Figure 3:
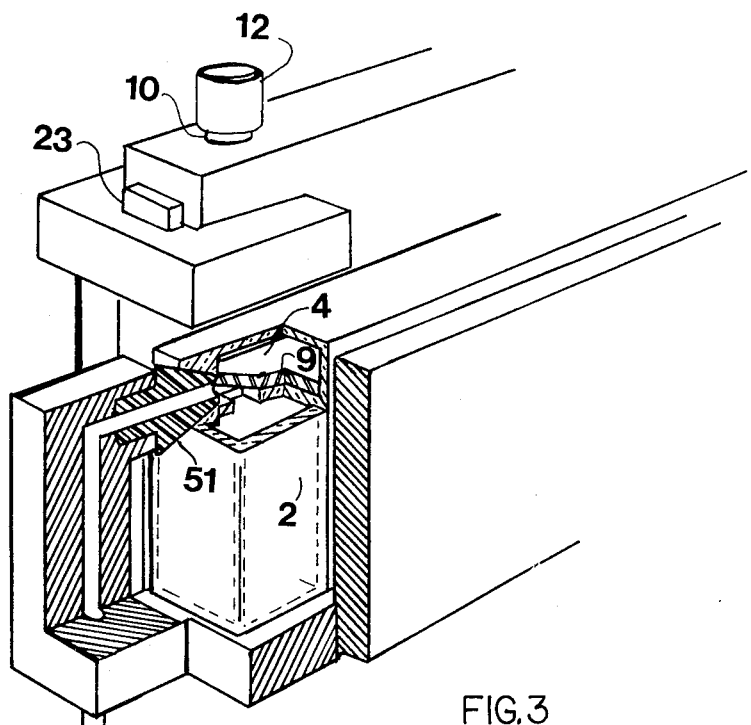
FIG. 3 is a partial perspective sectional detail of the pneumatic connection established between the cartridge and the detection module.
Figure 4:
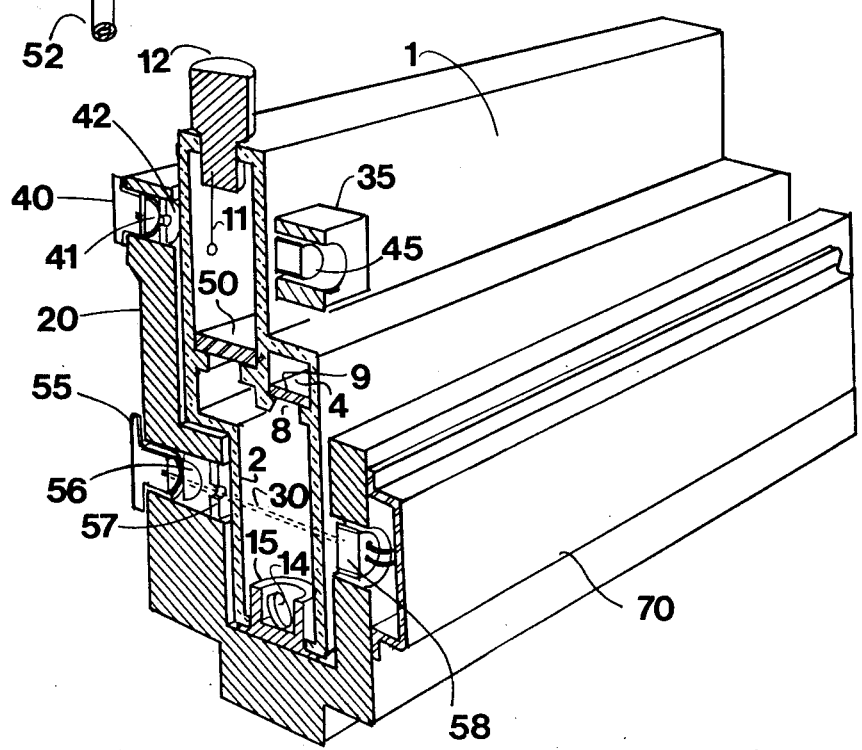
FIG. 4 is a sectional perspective view taken through the optical axis of the upper and lower optical systems of the cartridge detection module assembly.

Cartridge 3 is at this point ready for insertion into frame 20 of detection module 21 as illustrated in FIGS. 2, 3, and 4. Frame 20 can be fabricated of milling, casting or extruding aluminum or other light-weight metal. Placed on the exterior surface of cartridge 3 is code 23 which can be either in magnetic or optical ink or a coded panel of mechanically sensed depressions. Code 23 is in registration with and cooperates with appropriate sensors 32 mounted on frame 20 to instruct program control 34 (shown in FIG. 10) of the present invention as to the test that is to be made on the particular cartridge. Other information such as patient or sample identification can also be programmed for interpretation by sensors 32 so that detection module 21 can properly identify the cartridge for output calculation. In addition, sensors 32 start detection module 21 to place it into its operative state and to place cartridge 3 into the proper program sequence. All cartridges are scanned by the optical system at a nominal, pre-selected time interval.

Mounted within optical support member 35 of detection module 21 is the optical system for upper chamber 1 which comprises radiant energy or light source 40, collimated and condensed by lens 41 and aperture 42. The optical beam passes through the transparent wall of chamber 1 and the fluid specimen contained therein and then through the opposite wall of chamber 1 to fall onto the active surfae of inoculum photodetector 45. The media present in chamber 1 is evaluated by this optical system every interval until, for example, its turbidity reached a pre-selected value. The original insertion of cartridge 3 into detection module 21 indicates to program control 34 that the cell growth in chamber 1 is the only growth to be monitored since transfer to cuvettes 2 has not yet taken place. Photodetector 45 transmits an electric signal to inoculum detection amplifier 46 (shown in FIG. 10) which compares the turbidity or total change in turbidity in chamber 1 against the preselected value which corresponds to the desired cell concentration. When this concentration is reached, the photodetection amplifier 46 sends a switching signal to program control 34 which activates air or pneumatic system (solenoid) valves 49 of FIG. 10. Valves 49 supply a vacuum to tube 4 to create a pressure differential across valves 50 causing the latter to open to cause the fluid, e.g. bacterial suspension, in chamber 1 to flow into cuvettes 2 through orifice 8. Each of the valves 50 is unidirectional and is positioned in the floor of chamber 1 above each cuvette 2. Transfer of fluid occurs only when the pressure in chamber 1 is sufficiently high to separate the lower walls of each of valves 50 which walls are biased through vulcanization and sectional construction so as to normally remain in intimate engagement. After this transfer, cuvettes 2 are completely filled with fluid and the gas in each cuvette is displaced through orifices 8 and the walls of gas permeable tube 4 and then through pneumatic port 51 and the outlet tube 52 to the atmosphere or gas disposal means (not shown). Gas permeable tube 4 presents an effective liquid barrier to prevent passage of liquid.

Figure 7:
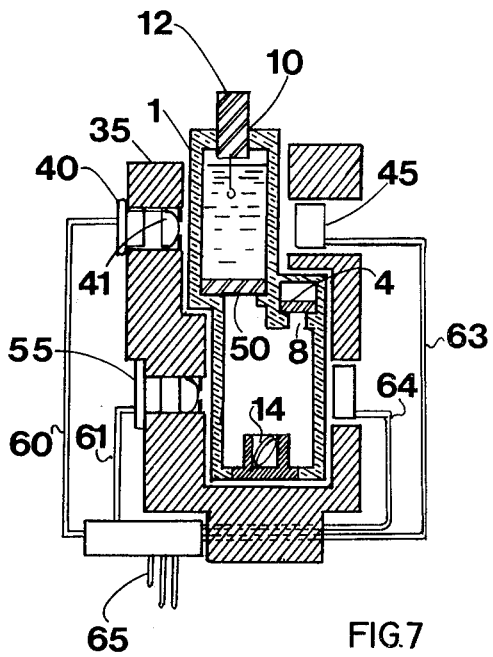
FIG. 7 illustrates a sectional elevation view taken along the optical axis of FIG. 4, with the sample fluid being shown in the upper chamber.
Figure 8:
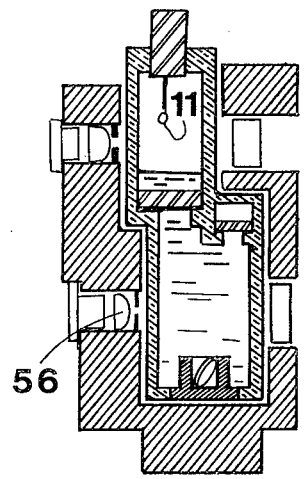
FIG. 8 is as recited in FIG. 7, but with the sample fluid being shown in the lower chamber.

FIG. 7 illustrates the condition of cartridge 3 during the period when chamber 1 is substantially filled with fluid and the optical beam of light source 40 is transilluminating its contents. FIG. 8 illustrates the condition of cartridge 3 during the end of the transfer showing valve 50 in its opened position and cuvettes 2 being completely filled with fluid. When this point is reached, the optical system for cuvettes 2 is enabled and light source 55 provides photon flux collimated by lens 56 and aperture 57 and transmitted through the transparent walls of cuvettes 2 and the fluid therein to fall onto the active surface of inoculum photodetector 58. Electrical leads 60 and 61 provide the contact between the program control 34 and light sources 40 and 55, respectively. Similarly leads 63 and 64 provide the contact between photodetector 45 and photodectection amplifier 46 and between photodetector 58 and photodetection amplifier (AMP) 66 which amplifies the signal from the multiplicity of cuvette photodetector elements of photodetector 58 respectively. Multiple lead cable 65 is provided for electrical leads 60, 61, 63 and 64. Shield 70 is mounted onto frame 20 over the photodetector 58 and electrical leads 63 and 64 of cuvettes 2.

Figure 11:
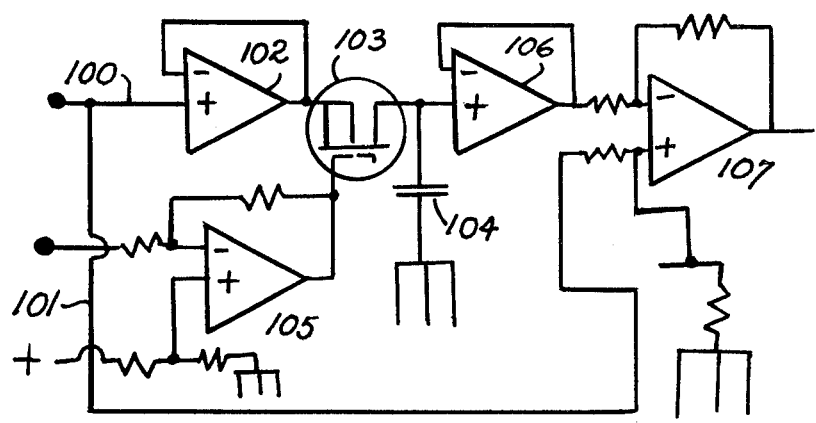
FIG. 11 is an electrical schematic diagram of the baseline correction module of FIG. 10.

For purposes of illustration, it is assumed that there are 10 cuvettes per cartridge. One of cuvettes 2 (cuvette no. 1) is filled with a completely arrested culture and is used as a blank for automatic gain control. Another cuvette which does not contain the antibiotic disc 14 is used as a control against which the growth rates of the organsims in the cuvettes containing the antibiotics can be compared and measured. Another function of the latter cuvette is to check the growth of the organism under normal growth conditions. If the control culture does not grow to achieve maximum turbidity, the program control will receive a signal of this condition. Sample and hold curcuit 69 receives the signal representing light passing through cuvette no. 1, which signal is evaluated against a reference value in the automatic gain control (AGC) error detector 90. The observation interval is approximately 1 second per cuvette in this example. During this period the amplitude of the signal is measured and automatic gain control (AGC) 72 and AGC error detector 70 compares the signal from cuvette no. 1 with the reference voltage and AGC 72 adjusts the gain on photodetection amplifier 66 so that the value of cuvette no. 1 equals this reference value. Since cuvette no. 1 contains an arrested culture, the maximum amount of light is tranmitted therethrough. Prior to the end of the reading period or interval for cuvette no. 1, the program control 34 signals the sample and hold circuit 69 for cuvettes 2 and retains the value derived therefrom. The gain of amplifier 66 will remain at this setting for the remainder of the sampling sequence within this detection module and cuvette array. Upon sequencing to the next cuvette cartridge that is inserted into the detection module, the gain will be readjusted appropriately as discussed above. Built into the signal amplifying system is a baseline correction module 80. Active filter 81 is positioned between baseline correction module 80 and amplifier 66. Immediately prior to the reading of the first cuvette, all light sources are off, and this correction circuit samples the dark baseline value and retains this value for subtraction from cuvette no. 1. Consequently the reading following this subtraction represents only the light induced signal. This circuit is operative in all individual readings by all detector elements. The activation of each light source is preceded by a brief dark period during which period the correction value is obtained, and consequently all effects of drift and ambient light are efficiently counteracted. Baseline correction module 80 performs a critical feature of the apparatus of the present invention and is described in detail in connection with FIG. 11.

Signals coming out of active filter 81, whose purpose is the reduction of noise, contain useful data plus baseline offset due to thermal drifts, ambient light, amplifier offsets and detector dark currents. It is the purpose of the baseline correction system to measure the offset prior to every reading and to retain it in a storage unit during the reading interval, subtracting it from the total signal containing both signal and offset.

The signal coming into the baseline correction module 80 splits into two paths, line 100 and line 101. Line 100 goes to buffer amplifier 102 whose output goes through a switching element 103, such as a MOSFET, to a storage capacitor 104. During the light off period, switch 103 is closed via ON signal from amplifier 105 on command from the program control 34. The signal out of amplifier 106 has the signal from line 101 subtracted from it, so that during the dark period, the output of amplifier 107 is essentially zero. Just prior to the end of the dark period, program control 34 via amplifier 105, opens the switch in element 103. The capacitor 104 now holds the value of voltage which was across it just prior to the opening of switch 103, as it has no substantial leakage paths to ground. When the light for a particular cuvette comes on, the value of voltage on the output of buffer amplifier 106, as read from the capacitor 104, as its input, remains constant and essentially represents the offset value of the data. Line 101 now contains signal plus offset. As the output of amplifier 106 contains the offset and as it subtracts from the data on line 101 via differential amplifier 107, the output of amplifier 107 contains only meaningful data since the offset is essentially cancelled out.

The signals coming from baseline correction module 80 then proceed via either logarithmic amplifier 112 or the scaling of logarithmic amplifier 102 or scaling amplifier 113 depends upon whether the detection module is set up for turbidimetry or nephelometry. Double pole switch 115 places either operation into the circuit. These operations or others including absorption are covered within the scope of the present invention.

The signal corresponding to cell concentration is converted from an analog voltage to a digital number in the analog-to-digital converter 114. The signal then goes to the digital computation system described more fully below. The basic computation consists of reading the turbidity of a control cuvette and of a cuvette containing antibiotic disc 14. The turbidity of each is read for two successive time intervals. Successive control concentrations can be represented by the symbols $C$, $C_{c1}$, $C_{c2}$ etc. Successive sample concentrations can be represented by the symbols $C_{s1}$, $C_{s2}$ etc. The growth rate ratio after two sucessive readings is defined as:

$$C_{s2} - C_{s1}/C_{c2} - C_{c1}$$

The computation section receives this ratio and assigns, for example, the different values to the result. Thus, the final result will always be one of ten values namely: 0.1, 0.2, 0.3, 0.4, 0.5. 0.6, 0.7, 0.8, 0.9, and 1.0. The lower the number, the greater is the effect the antibiotic has on the organism in a given test. A ratio of 1.0 would represent a completely resistant strain of organism.

The computation section comprises memory 116, memory input address and data transfer module 117 and memory output address and data transfer module 118 and computation system 119. The former 3 units of this section perform the function of retaining the previous reading for subtraction from the current reading. After the computation, the current reading is stored as well as the growth rate ratio that has just been computed while the previous reading is erased.

Change in the growth rate ratios from a completed computation for detection module 21 establishes the criteria for printing out data by means of printer control 121 on a signal from program control 34. As soon as the growth rate ratio changes by 0.1, the results will be printed out by printer 124. Auxiliary criteria can be inserted for terminating the test at a specific ratio change or a ratio change for one cuvette compared to the others. The printed output format may just be a serial listing of the ratios, or may include patient and/or sample identification numbers. Other more complex formats may include test identification and perhaps even antibiotic identification. Manual entry of additional data into the program may be made by optional data entry 195 which is electrically connected to printer control 121.

Data presentation is not limited to the above, but shall include such output devices as analog recorders, teletype machines, typewriters, facsimile recorders, cathode ray tube displays, computers and other computation devices.

Program control 34, contains all of the hard-wired sequencing functions utilized in the multiplexing light sources, responding to the computer signals, sample and hold control, basic system timing (clock function) malfunction monitoring and digital interfacing. The programming of the test sequence is not limited to the above, but will be the function of specific application of the apparatus of this invention.

The electro-optical section of the invention consists of multiple sets of light sources, lens, and detectors. On a cassette basic, all photodetectors are connected in parallel and may, without changing the function of the invention, be a long thin single photodetector or a series of photodetector elements deposited on a substrate as described above. The uniqueness of this part of the invention is that the photodetector elements are all connected in parallel, and the outputs from these elements all go to a common electronic preamplifying channel. The apparatus of the present invention refers to a multiplicity of detectors numbering greater than two and perhaps as many as two hundred in parallel. The invention does not exclude the case of several preamplifying electronic whose outputs are added into a common channel. It may be that for more than ten or twenty cuvettes separate preamplifiers are required. Herein, cost verses performance factors only influences the result. The light source described herein are solid state gallium arsenide phosphide light emitting diodes as manufactured by Fairchild, Monsanto and others, but are not limited to the type of light source. The light source may or may not contain the collimating lens. Where different wave-lengths are required, the use of tungsten type filament lamps, a plasma display type of lamps, or any of the class of light source which can be used economically in quantity are covered. Wave-length filters are used with tungsten sources to selectively allow narrow band-pass light to go through the solution.

Also covered within the scope of the present invention is the use of polarized light as a source and wherein the non-polarized light alone is detected on the premise that the light scattered by the particles in suspension comes off non-polarized. The non-polarized light quanta is proportional to the number of scattering particles in the path of the transmitted beam.

The light sources, in the invention, are multiplexed on and off at a rate such that the light from one has fully disappeared before the next light goes on. In fact, there is a dark period between light flashes wherein the baseline correction module samples the dark cuvette.

The electronic preamplifying channel will contain adequate filtering to pass the information pertaining to cell concentration and to reject non-related noise, drift, and the like. Active filter 81 performs this function as discussed above.

The program control 34 is a sequence control which controls virtually all the sequential functions of the apparatus of this invention and which monitors all the malfunctions and acts accordingly. Its function may be derived from an assemblage of discrete digital logic components or may be derived from a Read-Only-Memory as manufactured by Radiation, Inc., Fairchild, and others.

Photodetectors 45 and 58 may be of the photoconductive or photovoltaic or silicon photodiode variety as manufactured by Allen Bradley, Vactec and Solid State Radiation Inc., respectively.

Detection amplifiers 46 and 66 may be of the integrated high input impedance type. Amplifier 74 may be of a low noise hybrid type as manufactured by Philbrick Teledyne, Analog Devices and others. The scaling amplifier 83 may be of a type well known in the industry, for example, as manufactured by Fairchild, Motorola or Texas Instruments.

Figure 10:
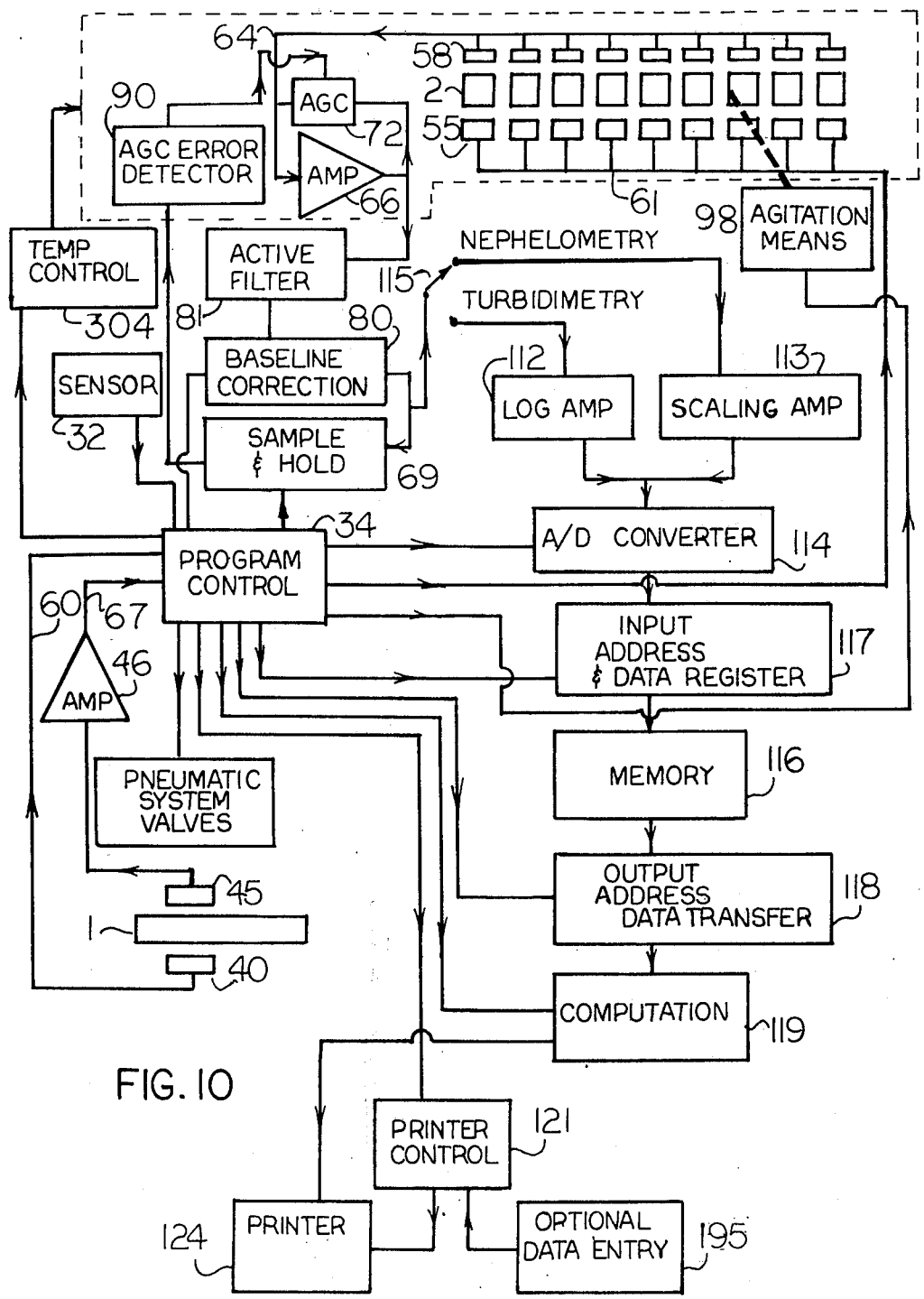
FIG. 10 is a functional block diagram of the electronic components required in the preferred embodiment.

The conversion of the analog data into printed numbers is accomplished by a combination of commerically available digital logic modules assembled to perform the function illustrated in FIG. 10, between the outputs of the log. amplifier 112 or scaling amplifier 113 and the printer 124, which may be a line printer such as one manufactured by Seiko, Monroe, Victor and others. This illustration of the invention herein does not preclude the use of a single, large scale integrated circuit, custom-made to perform the functions of the digital circuitry of FIG. 10. Digital logic modules to accomplish these tasks include Transitor-Transistor-Logic (TTL) as manufactured by Signetics, Fairchild, Texas Instruments and Motorola.

Analog to digital (A to D) converter 114, may be a 12 bit BCD converter as manufactured by Philbrick or Burr-Brown, Inc.

Memory unit 116 of the electronic computation means may consist of a multiple semiconductor memory as manufactured by Intel, Fairchild, Micro Systems, American Micro Systems, Inc. and others.

Figure 9:
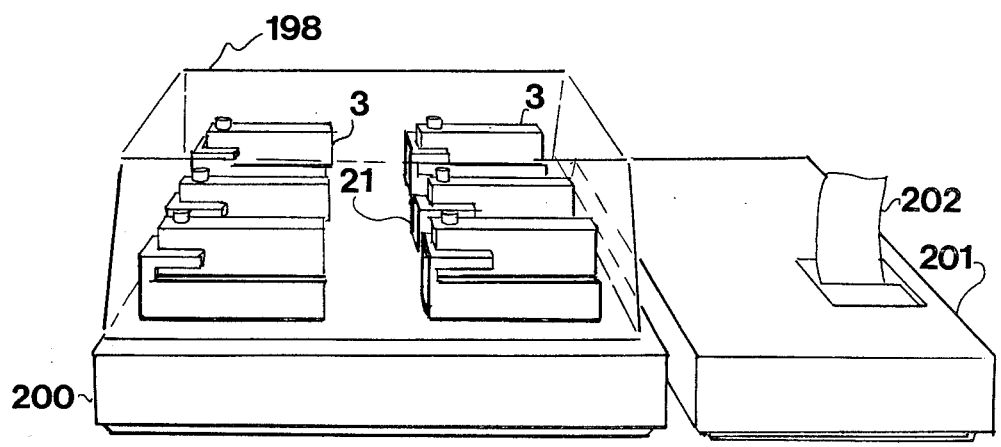
FIG. 9 illustrates a plurality of detection modules and cartridge as illustrated in FIG. 2 now embodied in a multiple configuration with an environmental control cover and control output components in an adjacent housing.

Referring now to FIG. 9, a plurality of cartridge 3 are shown inserted into a plurality of detection modules 21 and mounted under environmental control cover 198 of console 200. A gentle orbital motion is simultaneously applied to all of the detection modules 21 by means of agitation means 98 which is mounted within console 200 and is shown in FIG. 10. Agitation means 98 may be any well known electro-mechanical device such as an electric motor driven off-set cam which is electrically controlled by program control 34. The control output components illustrated in FIG. 10 are mounted within adjacent housing 201. The results of the output components can be read from printout 202.

The foregoing disclosure of this invention is not considered to be limiting since variations can be made by those skilled in the art without departing from the scope and spirit of the appended claims.

What we claim is:
1. A method of evaluating a biological fluid which comprises:
   a. placing the biological fluid into a chamber,
   b. placing an array of biological challenge materials into at least a portion of a plurality of cuvettes disposed below said chamber,
   c. monitoring the change in optical properties of said fluid in said chamber until the desired conditions of optical properties has been achieved,
   d. passing a finite portion of said fluid from said chamber into at least a portion of said cuvettes, at least one of which contains no biological challenge material, thereby producing an array of substantially identical fluid samples of known concentrations, and
   e. continually evaluating the change in rate of the optical properties of the fluid in the cuvette which does not contain biological challenge material and the optical properties of the fluid in at least one other cuvette which contains said biological challenge material, and thereby quantitatively determining the inhibitory concentration of said biological challenge material.

2. The method of claim 1 wherein said fluid from said chamber is passed through a liquid permeable membrane into said cuvettes until said cuvettes are substantially completely filled with said fluid.

3. The method of claim 1 wherein a pressure differential is imposed between said chamber for fluid and said cuvettes to thereby facilitate the flow of said fluid.

4. The method of claim 2 wherein a pressure differential is imposed between said chamber for fluid and said cuvettes to thereby facilitate the flow of said fluid.

5. A method of diagnostic analysis which comprises:
   a. placing a fluid containing microorganism into a chamber,
   b. introducing a diagnostic test material into at least one of a plurality of cuvettes disposed below said chamber,
   c. monitorting the change in optical properties of said fluid in said chamber until the desired optical properties has been achieved,
   d. passing a finite portion of said fluid from said chamber into at least a portion of said cuvettes, at least one of which contains no diagnostic test material, thereby producing an array of substantially identical fluid samples of known concentrations, and
   e. continually evaluating the change in rate of the optical properties of the fluid in the cuvette which does not contain diagnostic test material and the optical properties of the fluid in at least one other cuvette which contains said diagnostic test material, and thereby quantitatively determining the inhibitory concentration of said diagnostic test material.

6. The method of claim 5 wherein the fluid in said chamber is passed through a liquid permeable membrane into said cuvettes.

7. The method of claim 5 wherein said diagnostic test material is an anti-microbial agent.

8. The method of claim 6 wherein said diagnostic test material is an anti-microbial agent.

* * * * *